(12) United States Patent
Fehr

(10) Patent No.: US 8,227,630 B2
(45) Date of Patent: Jul. 24, 2012

(54) PROCESS FOR THE PREPARATION OF TETRANORLABDANE DERIVATIVES

(75) Inventor: Charles Fehr, Versoix (CH)

(73) Assignee: Firmenich SA, Geneva (CH)

(*) Notice: Subject to any disclaimer, the term of this patent is extended or adjusted under 35 U.S.C. 154(b) by 356 days.

(21) Appl. No.: 12/680,325

(22) PCT Filed: Oct. 20, 2008

(86) PCT No.: PCT/IB2008/054299
§ 371 (c)(1),
(2), (4) Date: Mar. 26, 2010

(87) PCT Pub. No.: WO2009/053884
PCT Pub. Date: Apr. 30, 2009

(65) Prior Publication Data
US 2011/0218347 A1    Sep. 8, 2011

(30) Foreign Application Priority Data
Oct. 23, 2007    (EP) .................................... 07119038

(51) Int. Cl.
*C07D 307/93*    (2006.01)
*C07C 33/14*    (2006.01)

(52) U.S. Cl. ........................ 549/458; 568/819

(58) Field of Classification Search ........................ None
See application file for complete search history.

(56) References Cited

FOREIGN PATENT DOCUMENTS
WO    WO 2006/010287 A1    2/2006
WO    WO 2007/010420 A1    1/2007

OTHER PUBLICATIONS

Daniewski et al., "High-Pressure Approach to the Total Synthesis of (±)-Ambreinolide and (±)-8-Epiambreinolide," J. Org. Chem., 50:3963-3965 (1985).
Erman et al., "The Rearrangement of Tertiary Propargyl Alcohols to $d,\beta$-Unsaturated Aldehydes in the Presence of Polymeric Organosilyl Vanadates," Tetrahedron Letters, 34:2981-2984 (1976).
Fehr et al., "Copper-Catalyzed Cycloisomerizations of 5-En-1-yn-3-ols," Organic Letters, 8(9):1839-1841 (2006).
Lorber et al., "Cis-dioxomolybdenum(VI) Complexes as New Catalysts for the Meyer-Schuster Rearrangement," Tetrahedron Letters, 37(6):853-856 (1996).
Nishizawa et al., "Total synthesis and morphogenesis-inducing activity of (±)-thallusin and its analogues," Tetrahedron Letters, 48:4229-4233 (2007).
Ohloff et al., "Significance of the Geminal Dimethyl Group in the Odor Principle of Ambrox®," Helvetica Chimica Acta, 68:2022-2029 (1985).
Verstegen-Haaksma et al., "Total Synthesis of (−)-Ambrox® from S-(+)-Carvone (part 6)," Tetrahedron, 50(33):10095-10106 (1994).
International Search Report and the Written Opinion of the International Searching Authority, Application No. PCT/IB2008/054299, Mar. 5, 2009.

*Primary Examiner* — Sun Jae Loewe
(74) *Attorney, Agent, or Firm* — Winston & Strawn LLP

(57) ABSTRACT

The present invention concerns a process for the preparation of a compound of formula (I) wherein the dotted line is a single bond and n is 1 or the dotted line is a double bond and n is 0, and wherein the relative configuration is as shown, in the form of any one of its diastereoisomers or enantiomers or mixtures thereof.

(I)

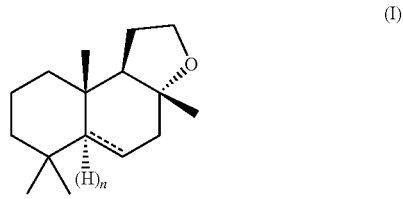

9 Claims, No Drawings

PROCESS FOR THE PREPARATION OF TETRANORLABDANE DERIVATIVES

This application is a 371 filing of International Patent Application PCT/IB2008/054299, filed Oct. 20, 2008.

TECHNICAL FIELD

The present invention relates to the field of organic synthesis and more specifically it concerns a process for the preparation of a compound of formula

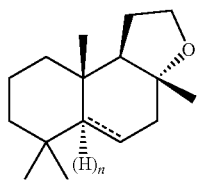

wherein the dotted line is a single bond and n is 1 or the dotted line is a double bond and n is 0, and wherein the relative configuration is as shown, in the form of any one of its diastereoisomers or enantiomers or mixtures thereof. The invention concerns also some of the starting compounds.

PRIOR ART

The compounds of formula (I) are very well known perfuming ingredients, some of which of particular relevance. Therefore, there is always a need for alternative synthesis to produce them.

Preparation of the compound (I) by cyclisation of compound (II) is a very attractive synthetic route, since atom economic and straightforward. Such approach has been illustrated in the prior art by:

G. Frater and co-workers in WO 06/10287, wherein an unsaturated alcohol similar to compound (II) is cyclised into the corresponding tetrahydrofuran in the presence of a protic mineral or organic acid (in the examples is used an excess of methanesulphonic acid in $CH_2Cl_2$ at room temperature, yield about 60%);

A. De Groot et al, in *Tetrahedron*, 1994, 50, 10095, wherein an unsaturated alcohol similar to compound (II) is cyclised into the corresponding tetrahydrofuran in the presence of para-toluenesulphonic acid in nitromethane at room temperature, yielding compound (I) in about 70% and with diastereomers; or by G. Ohloff et al, in *Helv. Chem. Acta*, 1985, 68, 2022, wherein an unsaturated alcohol similar to compound (II) is cyclised into the corresponding tetrahydrofuran in the presence of para-toluenesulphonic acid in nitromethane at 100° C., yielding compound (I), no yield indicated and not ratio between the various isomers.

However, the conditions reported in the prior art suffer from various problems that limit their use in industrial processes. Indeed they are not very environment friendly (excess of acids), provide the product in moderate yield, and/or require use of hazardous solvents such as nitromethane.

Therefore, there is still a need for alternative methods to perform such cyclisation and allow the use of more environmentally friendly conditions, and/or higher yields for instance and/or lower amounts of undesired isomers.

To the best of our knowledge, it is the first time that is reported an effective, cyclisation of an alcohol (II) into a compound (I).

DESCRIPTION OF THE INVENTION

We have now found that a compound of formula (I) as defined below, e.g. (3 aRS,9aRS,9bRS)-3a,6,6,9a-tetramethyl-1,2,3a,4,6,7,8,9,9a,9b-decahydronaphtho[2,1-b]furan or (3 aRS,9aRS,9bRS)-3a,6,6,9a-tetramethyl-1,2,3a,4,6,7,8,9,9a,9b-decahydronaphtho[2,1-b]furan, can be produced in an advantageous manner by means of a new and alternative method of cyclisation comprising an addition of an alcohol group on a carbon-carbon double bond.

Therefore, a first object of the present invention is a process for the preparation of a furan of formula (I), or (I')

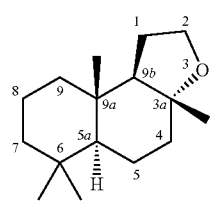

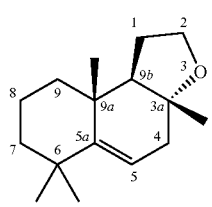

in the form of a racemic or optically active diastereoisomer, wherein the substituents in the positions 9a, 9b and 3a are in a relative configuration cis, and the hydrogen atom in position 5a and the oxygen atoms are in configuration trans relative to the methyl in position 9a;

comprising the cyclisation of an alcohol of formula (II), or respectively (II')

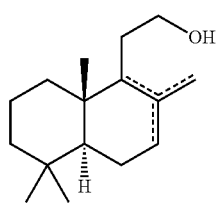

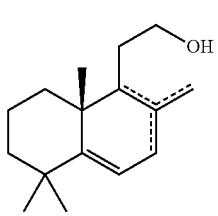

wherein the dotted lines indicate the presence of one carbon-carbon double bond in one of the indicated positions, said compounds (II) or (II') being in a racemic or optically active form and, in the case of compound (II), being also in the form of to diastereoisomer wherein the methyl in position 9a and the hydrogen atom in position 5a are in the relative trans configuration;

characterized in that said cyclisation is promoted by at least one Lewis acid and optionally an additive.

For the sake of clarity, it is understood that by the expression "in a racemic or optically active form" it is intended that the diastereoisomer (I), (I') or (II), or compound (II') respectively, has an enantiomeric excess (e.e.) ranging from 0 to 100%. For example a specific compound (I) can be in the form of any mixture of the two enantiomers of formulae (A) or (B)

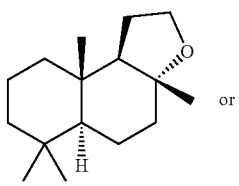
(A)

or

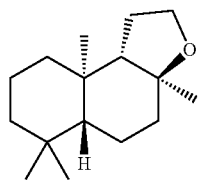
(B)

wherein the indicated stereochemistry is absolute.

As well known by a person skilled in the art, it is understood that when the invention's process is used to obtain a compound (I) or (I') in an optically active form, then the corresponding compounds (II) or (II') used as starting material or intermediates need to have an adequate optical activity.

As typical examples of compounds (I) one may cite the following:

(3aR,9aR,9bR)-3a,6,6,9a-tetramethyl-1,2,3a,4,6,7,8,9,9a,9b-decahydronaphtho[2,1-b]furan, (3aRS,9aRS,9bRS)-3a,6,6,9a-tetramethyl-1,2,3a,4,6,7,8,9,9a,9b-decahydronaphtho[2,1-b]furan, (3aS,9aS,9bS)-3a,6,6,9a-tetramethyl-1,2,3a,4,6,7,8,9,9a,9b-decahydronaphtho[2,1-b]furan, (3aR,5aS,9aS,9bR)-3a,6,6,9a-tetramethyldodecahydronaphtho[2,1-b]furan, (3aRS,5aSR,9aSR,9bRS)-3a,6,6,9a-tetramethyldodecahydronaphtho[2,1-b]furan or (3aS,5aR,9aR,9bS)-3a,6,6,9a-tetramethyldodecahydronaphtho[2,1-b]furan.

According to a particular embodiment of the invention, the invention's process is particularly useful for the preparation of compound (I') from the related compounds (II'), (III'), (IV') and (V').

According to a particular embodiment of the invention, the processes is carried out using a compound (II) or (II') of formula

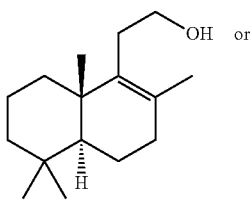
(III)

or

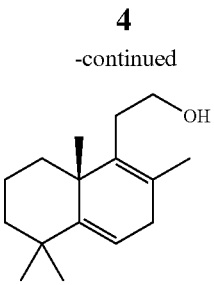
(III')

wherein the stereochemistry is defined as for compounds (II) or (II').

Compound (II) is a known compound, for instance see G. Frater and co-workers in WO 06/10287.

Compound (III) or (III') can be prepared from the known compounds (IV) or (IV') respectively

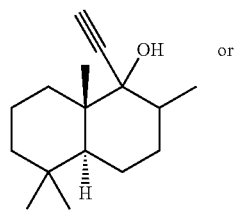
(IV)

or

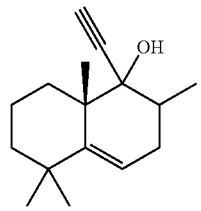
(IV')

wherein the stereochemistry is defined as for compounds (II) or (II'); and which are reported by C. Fehr et al., in *Org. Lett.*, 2006, 8, 1839, or by Danieswski et al. in *J. Org. Chem.*, 1985, 50, 3963. The enantiomerically pure compound (IV) or (IV') can be obtained according to the method reported in *Org. Lett.*, 2006, 8, 1839, and using an optically active precursor (disclosed in WO 07/010,420).

The compounds of formula (III') can thus be obtained by rearranging the propargylic alcohol (IV) or (IV') into the corresponding unsatured aldehyde (V) or (V')

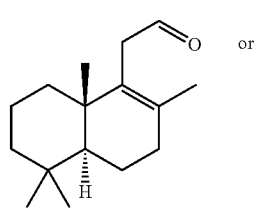
(V)

or

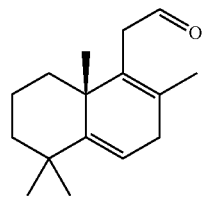
(V')

wherein the stereochemistry is defined as for compounds (II) or (II'); and reduction of the aldehyde yields the alcohols (III) or (III').

The propargylic rearrangement can be performed, for instance, using the conditions reported in Tet. Lett., 1996, 37, 853 or in Tet. Lett., 1976, 2981.

The reduction of the aldehyde into the alcohol can be performed, for instance, using a metal hydride such as $NaBH_4$ or $LiAlH_4$.

This approach is further illustrated in the examples.

The compounds of formula (II') or (III') are new compounds and are therefore, as valuable intermediates of the invention's process, another object of the present invention. Specific examples of said novel compounds are 2-(2,5,5,8a-tetramethyl-3,5,6,7,8,8a-hexahydro-1-naphthalenyl)ethanol.

As mentioned above, the invention's cyclisation is carried out by reacting compound (II) or (II') with at least one Lewis acid and optionally an additive.

Said Lewis acid can be used in stoechiometric or in catalytic amounts, relative to the starting alcohol.

Useful Lewis acids can be acidic clays, $BF_3$ derivatives or metal salts of formula, $AlCl_2R$, $MX_3$ or $ZnX_2$, wherein R is a $C_1$-$C_4$ alkyl group, M is a trivalent metal cation selected from the group consisting of Al, Y, Sc and Fe, and X represents a Cl or F atom or is a weakly or non-coordinating mono anion.

Said acids can be in an anhydrous form or for some of them also in a hydrate form. Furthermore, the boron or aluminum derivative, especially $BF_3$, could be in the form of any one of its adducts with an ether or carboxylic acid, such as $R^1{}_2O$ or $R^2COOH$, wherein $R^1$ is a $C_1$-$C_5$ alkyl group, such as $C_2H_5$ or $C_4H_9$, and $R^2$ is a $C_1$-$C_{20}$ alkyl group, such a methyl, ethyl or hept-3-yl.

Non-limiting examples of acidic clays are, for instance, clays of the F-20X type.

Non-limiting examples of suitable weakly or non-coordinating mono anions are $ClO_4{}^-$, $C_{1-8}$ sulfonates, $BF_4{}^-$, $PF_6{}^-$, $SbCl_6{}^-$, $AsCl_6{}^-$, $SbF_6{}^-$, $AsF_6{}^-$ or $BR^4{}_4{}^-$, wherein $R^4$ is a phenyl group optionally substituted by one to five groups such as halide atoms or methyl or $CF_3$ groups. According to a particular embodiment of the invention, X is $BF_4{}^-$, $PF_6{}^-$, $C_6F_5SO_3{}^-$, $CF_3SO_3{}^-$, $MeSO_3{}^-$, $MeC_6H_4SO_3{}^-$ or $Cl^-$.

According to a further particular embodiment of the invention, preferred Lewis acids are $BF_3$ or a $BF_3$ adduct with a $C_1$-$C_4$ ether or carboxylic acid (such as $Et_2O$, $Bu_2O$ or AcOH), $FeX_3$ or $ScX_3$, X being as defined above.

As specific examples, but not limiting, of Lewis acids one may cite acids such as $FeCl_3$, $Sc(CF_3SO_3)_3$, or $BF_3{}^-(Et_2O)_2$.

Additives can be used, e.g. to increase the selectivity and/or the yield of the cyclisation.

As additive can be used a $C_0$-$C_8$ sulphonic acid, water, a $C_1$-$C_{12}$ alcohol, silica, aluminium oxide or molecular sieves. According to a particular embodiment said additive can be acidic or neutral, and in the form of small particles, or even a powder.

Typical examples are butanol, neutral alumina, silica gel (e.g. of the type commonly used for chromatography), or molecular sieves 4 Å. Typical examples of sulphonic acids are $FSO_3H$, $MeSO_3H$, $MeC_6H_4SO_3H$ and the similar.

According to a particular embodiment, for the cyclisation a combination of $FeCl_3$ and silica can be used. Alternatively a combination of $FeCl_3$ and $C_0$-$C_8$ sulphonic acid or a combination of $FeCl_3$ and butanol can be used.

The Lewis acid can be added to the reaction medium in a large range of concentrations. As non-limiting examples, one can cite catalyst concentrations ranging from 0.01 to 1.50 molar equivalents, relative to the molar amount of the starting alcohol (II) or (II'). Preferably, the Lewis acid concentration will be comprised between 0.1 and 0.6 molar equivalents. It goes without saying that the optimum concentration of acid will depend on the nature of the latter and on the desired reaction time.

The additive can be added to the reaction medium in a large range of concentrations. As non-limiting examples, one can cite additive concentrations ranging from 10 to 250%, relative to the weight of the Lewis acid. Preferably, the additive concentration will be comprised between 10 and 120%, relative to the weight of the Lewis acid.

The cyclisation of the present invention in any of its embodiments can be carried out in the presence or in the absence of solvent, but in any case it is advantageously performed under anhydrous conditions.

However, according to a preferred embodiment of the invention, the process is advantageously carried out in the presence of a solvent. A suitable solvent is one which is aprotic. Non-limiting examples of such a solvent are ethers, esters, amides, aromatic hydrocarbons, linear or branched or cyclic hydrocarbons, chlorinated solvents (in particular chlorinated hydrocarbon) and mixtures thereof. More preferably, the solvent is a methylene chloride, 1,2-dichloroethane, 1,2-dichlorobenzene, toluene and mixtures thereof. According to another embodiment of the invention, the reaction is carried out in a solvent or mixture of solvents having a dielectric constant below 25, at standard conditions (as indicated in the Handbook of Chemistry and Physics, 87$^{th}$ edition, 2006-2007).

The temperature, at which this process of the invention can be carried out, in any of its embodiments, is comprised between −50° C. and 140° C., preferably between −10° C. and 80° C. Of course a person skilled in the art is also able to select the preferred temperature as a function of the melting and boiling point of the starting and final products and/or an eventual solvent.

EXAMPLES

The invention, in all its embodiments, will now be described in further detail by way of the following examples, wherein the abbreviations have the usual meaning in the art, the temperatures are indicated in degrees centigrade (° C.); the NMR spectral data were recorded in $CDCl_3$ with a 360 MHz or 100 MHz machine for $^1H$ or $^{13}C$ respectively, the chemical displacements δ are indicated in ppm with respect to TMS as standard, the coupling constants J are expressed in Hz.

Example 1

A) Preparation of 2-(2,5,5,8a-tetramethyl-3,5,6,7,8,8a-hexahydro-1-naphthalenyl)ethanol (1)

Step A)

A solution of 1-ethynyl-2,5,5,8a-tetramethyl-1,2,3,5,6,7,8,8a-octahydro-1-naphthalenol (4.00 g; 17.2 mmol) in o-xylene (60 ml) was treated with $[V_2O_6SiPh_2]_n$, (400 mg) [Tetrahedron Lett. 1976, 17, 2981] and heated at reflux (145° C.). After 17 hours, the rearrangement was completed. The reaction mixture was poured into 5% aqueous NaOH. The product was extracted twice with $Et_2O$ and washed successively with $H_2O$ and twice with satured aqueous NaCl, dried ($Na_2SO_4$) and evaporated. Bulb-to-bulb distillation (125° C. (oven temp.)/0.04 mbar) afforded 97% pure (2,5,5,8a-tetramethyl-3,5,6,7,8,8a-hexahydro-1-naphthalenyl)acetaldehyde (3.42 g; yield=83%).

$^1$H-NMR: 1.13 (s, 3H), 1.14 (s, 3H), 1.77 (s, 3H), 1.10-1.35 (m, 2H), 1.42-1.60 (m, 2H), 1.65 (s, 3H), 1.70-1.85 (m, 2H), 2.62-2.72 (m, 2H), 3.11 (d, J=17 Hz, 1H), 3.22 (d, J=17 Hz, 1H), 5.66 (m, 1H), 9.55 (t, J=2 Hz, 1H).

$^{13}$C-NMR: 201.4 (d), 148.3 (s), 129.6 (s), 129.4 (s), 117.1 (d), 43.3 (t), 40.6 (t), 39.2 (s), 37.5 (t); 36.1 (s), 33.6 (t), 32.8 (q), 30.5 (q); 25.8 (q), 19.6 (q), 18.7 (t).

Step B)

A solution of (2,5,5,8a-tetramethyl-3,5,6,7,8,8a-hexahydro-1-naphthalenyl)acetaldehyde obtained in step A) (3.40 g; 14.2 mmol) in Et$_2$O (10 ml) was added drop-wise to a stirred suspension of LiAlH$_4$ (410 mg; 10.7 mmol) in Et$_2$O (20 ml) at such a rate that a gentle reflux was maintained (5 minutes). The suspension was heated at reflux for 30 minutes, cooled at 0° C. and treated successively drop-wise with water (0.4 ml), 5% aqueous NaOH (0.4 ml) and water (3×0.4 ml). After stirring for 5 minutes at room temperature the suspension was filtered over Celite and the filtrate concentrated. Bulb-to-bulb distillation (130° C. (oven temp.)/0.03 mbar) afforded pure 2-(2,5,5,8a-tetramethyl-3,5,6,7,8,8a-hexahydro-1-naphthalenyl)ethanol (1) (3.21 g; yield=90%).

$^1$H-NMR: 1.12 (s, 3H), 1.14 (s, 3H), 1.16 (s, 3H), 1.22-1.38 (m, 2H), 1.45 (m, 1H), 1.55 (m, 1H), 1.70 (s, 3H), 1.72-1.85 (m, 2H), 1.91 (m, 1H), 2.30 (m, 1H), 2.51 (m, 1H), 2.52-2.65 (m, 2H), 3.63 (m, 2H), 5.63 (m, 1H).

$^{13}$C-NMR: 149.0 (s), 133.8 (s), 127.0 (s), 117.1 (d), 62.6 (t), 40.7 (t), 39.5 (s), 37.0 (t), 36.0 (s); 33.5 (t), 32.8 (q), 31.6 (t), 30.9 (q); 26.0 (q), 19.6 (q), 18.8 (t).

B) Preparation of 2-(2,5,5,8aβ-tetramethyl-3,4,4aα,5,6,7,8,8a-octahydro-1-naphthalenyl)ethanol (2)

Step A)

A solution of 1-ethynyl-2,5,5,8a-tetramethyl-perhydro-4aH-1-naphthalenol (8.48 g; 92% pure; 33.3 mmol) in o-xylene (40 ml) was added drop-wise in 20 minutes to a refluxing mixture (145° C.) of [Ph$_3$SiO]$_3$VO (1.79 g; 2.00 mmol), triphenylsilanol (1.38 g; 5.00 mmol) and stearic acid (191 mg; 0.67 mmol) in o-xylene (40 ml). After 7 hours the reaction mixture was poured into 5% aqueous NaOH. The product was extracted twice with Et$_2$O and washed successively with H$_2$O and twice with saturated aqueous NaCl, dried (Na$_2$SO$_4$) and evaporated. Bulb-to-bulb distillation (125° C. (oven temp.)/0.03 mbar) afforded 87% pure (2,5,5,8aβ-tetramethyl-3,4,4aα,5,6,7,8,8a-octahydro-1-naphthalenyl)acetaldehyde (7.59 g; yield=85%).

Using [V$_2$O$_6$SiPh$_2$]$_n$ also afforded (2,5,5,8aβ-tetramethyl-3,4,4aα,5,6,7,8,8a-octahydro-1-naphthalenyl)acetaldehyde in 85% yield.

$^{13}$C-NMR: 201.5 (d), 132.1 (s), 131.3 (s), 51.7 (d), 43.2 (t), 41.5 (t), 38.5 (s), 37.2 (t), 33.9 (t); 33.3 (s), 33.2 (q), 21.6 (q), 19.9 (q); 19.8 (q), 18.9 (t), 18.9 (t).

Step B)

A solution of (2,5,5,8aβ-tetramethyl-3,4,4aα,5,6,7,8,8a-octahydro-1-naphthalenyl)acetaldehyde (7.58 g; 87% pure; 28.2 mmol) in Et$_2$O (50 ml) was added drop-wise to a stirred suspension of LiAlH$_4$ (800 mg; 21.1 mmol) in Et$_2$O (20 ml) at such a rate that a gentle reflux was maintained (5 minutes). The suspension was heated at reflux for 30 minutes, cooled at 0° C. and treated successively drop-wise with water (0.8 ml), 5% aqueous NaOH (0.8 ml) and water (3×0.8 ml). After stirring for 5 minutes at room temperature, the white suspension was filtered over Celite and the filtrate concentrated. Bulb-to-bulb distillation (130° C. (oven temp.)/0.03 mbar) afforded 94% pure 2-(2,5,5,8aβ-tetramethyl-3,4,4aα,5,6,7,8,8a-octahydro-1-naphthalenyl)ethanol (2) (6.98 g; 94% pure; yield=99%).

$^{13}$C-NMR: 136.2 (s), 128.6 (s), 62.7 (t), 51.7 (d), 41.7 (t), 38.7 (s), 37.2 (t), 33.7 (t), 33.3 (s); 33.3 (q), 31.5 (t), 21.7 (q), 20.1 (q); 19.9 (q), 19.0 (t), 19.0 (t).

Example 2

A) Cyclisation of 2-(2,5,5,8aβ-tetramethyl-3,4,4aα,5,6,7,8,8a-octahydro-1-naphthalenyl)ethanol (2)

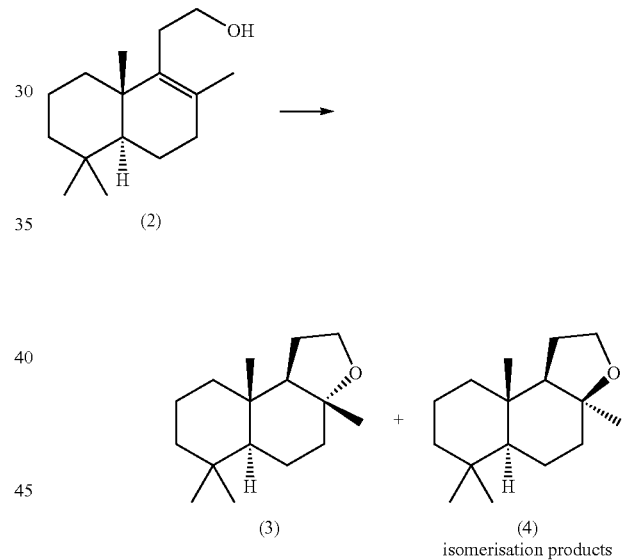

(3)  (4)
isomerisation products

Using FeCl$_3$ and SiO$_2$:

A solution of 2-(2,5,5,8aβ-tetramethyl-3,4,4aα,5,6,7,8,8a-octahydro-1-naphthalenyl)ethanol (2) (500 mg; 94% pure; 1.99 mmol) in 1,2-dichloroethane (5 ml) and CH$_2$Cl$_2$ (8 ml) was treated at 24° C. with SiO$_2$ 60 Å (70-220 µm) (81 mg). Under stirring anhydrous FeCl$_3$ (162 mg; 1.00 mmol) was added. After 20 minutes the dark reaction mixture was poured under stirring into 5% aqueous HCl and was extracted twice with Et$_2$O. The organic phase was washed successively with water, sutured aqueous NaHCO$_3$ and twice with saturated aqueous NaCl e, dried (Na$_2$SO$_4$) and evaporated (513 mg). Bulb-to-bulb distillation (125° C. (oven temp.)/0.06 mbar) afforded (3) (481 mg; 77% pure; yield=79%), containing recovered (2) (yield=13%).

B) Cyclisation of 2-(2,5,5,8a-tetramethyl-3,5,6,7,8,8a-hexahydro-1-naphthalenyl)ethanol (1)

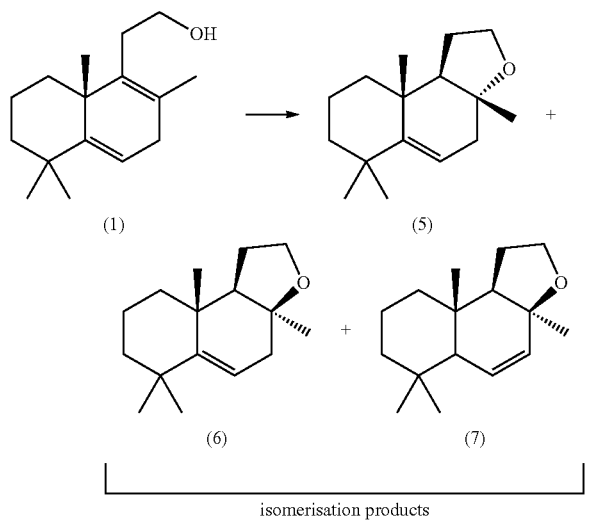

isomerisation products

Using FeCl$_3$ and SiO$_2$:

A solution of 2-(2,5,5,8a-tetramethyl-3,5,6,7,8,8a-hexahydro-1-naphthalenyl)ethanol (1) (500 mg; 96% pure; 2.05 mmol) in 1,2-dichloroethane (5 ml) and CH$_2$Cl$_2$ (8 ml) was treated at 24° C. with SiO$_2$ 60 Å (70-220 µm) (84 mg). Under stirring FeCl$_3$ (glove-box stored; 167 mg; 1.03 mmol) was added. After 20 min the dark reaction mixture was poured under stirring into 5% HCl and was extracted with Et$_2$O (2×). The organic phase was washed successively with water, sat. aq. NaHCO$_3$ and saturated aqueous NaCl, dried (Na$_2$SO$_4$) and evaporated. Bulb-to-bulb distillation (125° C. (oven temp.)/0.06 mbar) afforded (±)-(5) (454 mg; 81% pure; yield=73%). It was also obtained (6) (yield=4%) and (7) (yield=2%).

It was also recovered (1) (yield=8%).

Using FeCl$_3$ in Stoichiometric Amounts:

A solution of 2-(2,5,5,8a-tetramethyl-3,5,6,7,8,8a-hexahydro-1-naphthalenyl)ethanol (300 mg; 1.28 mmol) in CH$_2$Cl$_2$ (4 ml) and 1,2-dichloroethane (2 ml) was treated at 0° C. with FeCl$_3$ (208 mg; 1.28 mmol). After 40 minutes the conversion was completed. The reaction mixture was poured under stirring into 5% aqueous HCl and was extracted twice with Et$_2$O. The organic phase was washed successively with water, saturated aqueous NaHCO$_3$ and twice with saturated aqueous NaCl, dried (Na$_2$SO$_4$) and evaporated. Bulb-to-bulb distillation (115° C. (oven temp.)/0.03 mbar) afforded pure (±)-(5) (198 mg; 96% pure; yield=63%) containing traces of (6) (yield=2%).

Using FeCl$_3$ in Catalytic Amounts:

A solution of (+)-2-(2,5,5,8a-tetramethyl-3,5,6,7,8,8a-hexahydro-1-naphthalenyl)ethanol* ([α]$_D^{20}$+45 (CHCl$_3$; c: 0.84; 1.0 g; 4.27 mmol) in 1,2-dichloroethane (20 ml) was treated at 0° C. with anhydrous FeCl$_3$ (138 mg; 0.848 mmol). After 2 minutes, the temperature was allowed to reach room temperature. Stirring was to continued for 3 hours, then another portion of anhydrous FeCl$_3$; (69 mg; 0.424 mmol) was added and stirring continued for 30 minutes. The reaction mixture was stopped at partial conversion by pouring it under stirring into 5% aqueous HCl and was extracted twice with Et$_2$O. The organic phase was washed successively with water, saturated aqueous NaHCO$_3$ and twice with saturated aqueous NaCl, dried (Na$_2$SO$_4$) and evaporated. Purification by column chromatography (SiO$_2$ (60 g); cyclohexane/AcOEt=99:1), afforded 159 mg of first fractions (containing appreciatively 39% of (+)-(5), 27% of (6) and 9% of (+)-(7)), followed by 423 mg (yield=42%) of pure (+)-(5) (93% ee; [α]$_D^{20}$+84 (CHCl$_3$; c: 0.92; 739 mg) and then using cyclohexane/AcOEt=9:1, 316 mg (yield=32%) of (+)-(1) were recovered.

*prepared from (−)-2-methyl-4-(2,6,6-trimethyl-1-cyclohexen-1-yl)butanal prepared according the procedure described in WO 2007/010420

Example 3

Following the same experimental procedure as described in Example 2, other Lewis acids have been tested.

The results for the cyclisation of (2) are reported in the following Table I:

| N° | Lewis acid[1] | Additive[2] | Solvent[3] | T (° C.) | t[4] | Res.[5] | (2)[6] | (3)[6] | (4)[6] | (3)/(4)[7] |
|---|---|---|---|---|---|---|---|---|---|---|
| 1 | SC(OTf)$_3$ (0.2) | — | CH$_2$Cl$_2$ | 20 | 6 h. | | 60 | 30 | 0 | >100 |
| 2 | FeCl$_3$ (0.25) | — | (ClCH$_2$)$_2$ | 20 | 3 h | | 32 | 57 | 1 | 57 |
| 3 | FeCl$_3$ (0.50) | — | (ClCH$_2$)$_2$ CH$_2$Cl$_2$ (½) | 10 | 3 h | 23 | 11 | 78 | 0 | >100 |
| 4 | FeCl$_3$ (0.50) | SiO$_2$ (50%) | (ClCH$_2$)$_2$ CH$_2$Cl$_2$ (½) | 20 | 20 min | 6 | 11 | 77 | 1 | 77 |
| 5 | FeCl$_3$ (0.50) | SiO$_2$ (50%) | toluene | 20 | 2 h. | 6 | 13 | 74 | 2 | 37 |
| 6* | MeSO$_3$H (1.28) | — | CH$_2$Cl$_2$ | 0° | 20 min | 12 | 2 | 81 | 5 | 16 | p.s. it was used the starting material obtained in Example 1 (94% purity)
[1] between brackets is the molar amount relative to starting alcohol (2)
[2] between brackets is the w/w amount relative to Lewis acid
[3] the w/w ratio between (2) and the solvent is the same as in Example 2, between brackets it is the w/w ratio between two solvents
[4] reaction time
[5] non-volatile products recovered other than (2), (3) and (4), w/w percentage relative to the amount of (2) initially used (%)
[6] relative amounts obtained by GC analysis of the volatile fraction (%)
[7] molar ratio
OTf = triflate-*: comparative example (prior art conditions-WO 06/10287)

It is evident from said Table I that the invention's process is able to deliver yields as good as those obtainable by the use of the standard method (a strong protic acid only), and in addition the invention's process allows to obtain the desired product with a much higher selectivity compared to the one allowed by the use of a strong protic acid only.

The results for the cyclisation of a mixture of isomers of formula (II) (ambrols) are reported in the following Table II:

| N° | Lewis acid[1] | Additive[2] | Solvent[3] | T (°C.) | t[4] | Res.[5] | SM[6] | (3)[6] | (4)[6] | (3)/(4)[7] |
|---|---|---|---|---|---|---|---|---|---|---|
| 1 | FeCl$_3$ (0.50) | SiO$_2$ (50%) | (ClCH$_2$)$_2$ | 20 | 40 min. | 3 | 18 | 73 | 4 | 18 |
| 2 | FeCl$_3$ (0.2) | MeSO$_3$H (0.2)** | (ClCH$_2$)$_2$ CH$_2$Cl$_2$ (½) | 20 | 10 min. | 2 | 9 | 79 | 6 | 13 |
| 3 | MeSO$_3$H (1.28) | — | CH$_2$Cl$_2$ | 20 | 45 min. | 8 | 23 | 67 | 6 | 11 |

SM: starting alcohol
[1] between brackets is the molar amount relative to starting alcohol
[2] between brackets is the w/w amount relative to Lewis acid;
**molar amount relative to starting alcohol
[3] the w/w ratio between SM and the solvent is the same as in Example 2), between brackets it is the w/w ratio between two solvents
[4] reaction time
[5] non-volatile products recovered other than starting alcohol, (3) and (4), w/w percentage relative to the amount of alcohol initially used (%)
[6] relative amounts obtained by GC analysis of the volatile fraction (%)
[7] molar ratio
OTf = triflate-*: comparative example (prior art conditions-WO 06/10287)

It is evident from said Table II that, by using a mixture of ambrols, the invention's process is able to deliver yields higher than those obtainable by the use of the standard method (a strong protic acid only), and with significantly higher selectivities than the one obtained by the use of a strong protic acid only.

The results for the cyclisation of a mixture of isomers of formula (II) (ambrols) are reported in the following Table III:

| N° | Lewis acid[1] | Additive[2] | Solvent[3] | T (°C.) | t[4] | SM[5] | (3)[5] | (4)[5] | (3)/(4)[6] |
|---|---|---|---|---|---|---|---|---|---|
| 1 | FeCl$_3$ (0.50) | SiO$_2$ (50%) | MeNO$_2$ | 20 | 30 min. | 30 | 46 | 7 | 6.5 |
| 2 [8] | TsOH[7] (2.0) | — | MeNO$_2$ | 20 | 60 min. | 60 | 33 | 3.5 | 9.5 |
| 3 | TsOH (2.0) | — | MeNO$_2$ | 20 | 24 h. | 15 | 57 | 24 | 2.4 |

SM: starting alcohol
[1] between brackets is the molar amount relative to starting alcohol
[2] between brackets is the w/w amount relative to Lewis acid; ** molar amount relative to starting alcohol
[3] the w/w ratio between SM and the solvent is the same as in Example 2), between brackets it is the w/w ratio between two solvents
[4] reaction time
[5] relative amounts obtained by GC analysis of the volatile fraction (%)
[6] molar ratio
[7] TsOH is MeC$_6$H$_4$SO$_3$H
[8] reaction was not finished.

It is evident from said Table III that the invention's process is much faster than the prior art process, since it is finished in only 30 minutes, to give industrially interesting conversions. Furthermore, at the end of the conversion, it is also evident that the invention's process, although giving slightly lower amounts of the desired product, allows much higher selectivity than the one obtained by the use of a strong protic acid only.

The results for the cyclisation of (1) are reported in the following Table IV:

| N° | Lewis acid[1] | Additive[2] | Solvent[3] | T (°C.) | t[4] | (1)[5] | (5)[5] | (6) + (7)[5] |
|---|---|---|---|---|---|---|---|---|
| 1 | FeCl$_3$ (0.25) | — | (ClCH$_2$)$_2$ | 20 | 3.5 h. | 7 | 68 | 11 |
| 2 | FeCl$_3$ (0.50) | SiO$_2$ (50%) | (ClCH$_2$)$_2$ CH$_2$Cl$_2$ (½) | 20 | 20 min. | 8 | 81 | 6 |
| 3 | Sc(OTf)$_3$ (0.2) | — | CH$_2$Cl$_2$ | 20 | 3 h. | 21 | 56 | 12 |
| 4 | BF$_3$(OEt)$_2$ (1.1) | — | CH$_2$Cl$_2$ | 20 | 4 h. | 29 | 61 | 4 | p.s. it was used the starting material obtained in Example 1 (94% purity)
[1] between brackets is the molar amount relative to starting alcohol (2)
[2] between brackets is the w/w amount relative to Lewis acid
[3] the w/w ratio between (2) and the solvent is the same as in Example 2), between brackets it is the w/w ratio between two solvents
[4] reaction time
[5] relative amounts obtained by GC analysis of the volatile fraction (%)
OTf = triflate When the cyclisation of (1) with MeSO$_3$H (prior art conditions—WO 06/10287) was attempted (1.3 molar equivalent, T 20° C.) a very complex mixture was obtained, wherein the desired furan (5) accounted for less than 5% of the total and many unknown products were obtained (accounting for more than 30%).

The same cyclisation with ClSO$_3$H (1.0 molar equivalent, T −78° C., MeNO$_2$) afforded only a rearrangement product (3a,5a,6,6-tetramethyl-1,2,3a,4,5,5a,6,7,8,9-perhydronaphtho[2,1-b]furan) in about 25% yield.

What is claimed is:

1. A process for the preparation of a furan of formula (I), or (I')

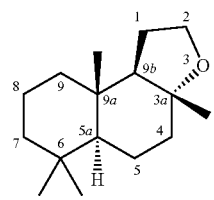
(I)

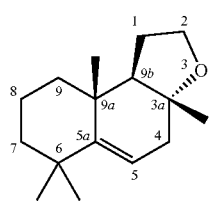
(I')

in the form of a racemic or optically active diastereoisomer, wherein the substituents in the positions 9a, 9b and 3a are in a relative configuration cis, and the hydrogen atom in position 5a and the oxygen atoms are in configuration trans relative to the methyl in position 9a;
which comprises cyclizing an alcohol of formula (II), or respectively (II')

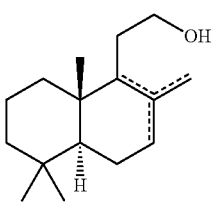
(II)

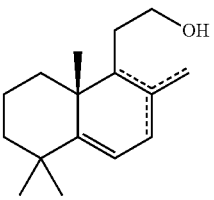
(II')

wherein the dotted lines indicate the presence of one carbon-carbon double bond in one of the indicated positions, said compounds (II) or (II') being in a racemic or optically active form and, in the case of compound (II), being also in the form of diastereoisomer wherein the methyl in position 9a and the hydrogen atom in position 5a are in the relative trans configuration;
while promoting the cyclizing with at least one Lewis acid selected from the group consisting of (a) metal salts of formula $AlCl_2R$ or $MX_3$, wherein R is a $C_1$-$C_4$ alkyl group, M is a trivalent metal cation selected from the group consisting of Al, Y, Sc and Fe, and X represents a Cl or F atom or is a weakly or non-coordinating mono anion selected from the group consisting of $ClO_4^-$, $C_{1-8}$ sulfonates, $BF_4^-$, $PF_6^-$, $SbCl_6^-$, $AsCl_6^-$, $SbF_6^-$, $AsF_6^-$ or $BR_4^{4-}$, $C_6F_5SO_3^-$, $CF_3SO_3^-$, $MeSO_3^-$, $MeC_6H_4SO_3$, wherein $R^4$ is a phenyl group optionally substituted by one to five groups of halide atoms or methyl or $CF_3$ groups, and (b) $BF_3$ adducts with an $(OR^1)_2$ or $R^2COOH$, wherein $R^1$ is a $C_1$-$C_5$ alkyl group, and $R^2$ is a $C_1$-$C_{20}$ alkyl group, wherein the cyclizing is optionally conducted with an additive to assist in increasing selectivity or yield of the cyclizing.

2. The process according to claim 1, wherein the compounds (II) or (II') are respectively of formula (III) or (III')

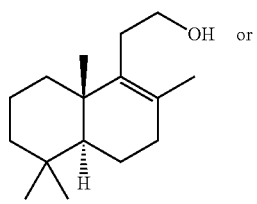
(III)

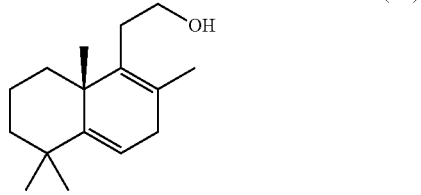
(III')

wherein the stereochemistry is defined as for compounds (II) or (II').

3. The process according to claim 1, wherein the compound of formula (I) or (I') is optically active.

4. The process according to claim 1, wherein the compound of formula (I) or (I') is:
(3aR,9aR,9bR)-3a,6,6,9a-tetramethyl-1,2,3a,4,6,7,8,9,9a,9b-decahydronaphtho[2,1-b]furan,
(3aRS,9aRS,9bRS)-3a,6,6,9a-tetramethyl-1,2,3a,4,6,7,8,9,9a,9b-decahydronaphtho[2,1-b]furan,
(3aS,9aS,9bS)-3a,6,6,9a-tetramethyl-1,2,3a,4,6,7,8,9,9a,9b-decahydronaphtho[2,1-b]furan,
(3aR,5aS,9aS,9bR)-3a,6,6,9a-tetramethyldodecahydronaphtho[2,1-b]furan,
(3aRS,5aSR,9aSR,9bRS)-3a,6,6,9a-tetramethyldodecahydronaphtho[2,1-b]furan, or
(3aS,5aR,9aR,9bS)-3a,6,6,9a-tetramethyldodecahydronaphtho[2,1-b]furan.

5. The process according to claim 1, wherein said weakly or non-coordinating mono anion is selected from the group consisting of $ClO_4^-$, $C_{1-8}$ sulfonates, BF4-, PF6-, SbCl6-, AsCl6-, SbF6-, AsF6- or $BR_4^{4-}$, wherein $R^4$ is a phenyl group optionally substituted by one to five groups of halide atoms or methyl or $CF_3$ groups.

6. The process according to claim 1, wherein X is BF4-, PF6-, $C_6F_5SO_3^-$, $CF_3SO_3^-$, $MeSO_3^-$, $MeC_6H_4SO_3^-$ or Cl-.

7. The process according to claim 1, wherein the Lewis acid is $FeCl_3$, $Sc(CF_3SO_3)_3$, or $BF_3(OEt)_2$.

8. The process according to claim 1, which is conducted by reacting compound (II) or (II') with the Lewis acid and at least one additive of a $C_0$-$C_8$ sulphonic acid, water, a $C_1$-$C_{12}$ alcohol, silica, aluminium oxide or molecular sieves.

9. The process according to claim 8, wherein the Lewis acid is $FeCl_3$ and the additive is a $C_0$-$C_8$ sulphonic acid, butanol or silica.

* * * * *

UNITED STATES PATENT AND TRADEMARK OFFICE
CERTIFICATE OF CORRECTION

PATENT NO. : 8,227,630 B2  
APPLICATION NO. : 12/680325  
DATED : July 24, 2012  
INVENTOR(S) : Fehr Page 1 of 1

It is certified that error appears in the above-identified patent and that said Letters Patent is hereby corrected as shown below:

Column 13:  
Line 64, change "$BF_4^-$, $PF_6^-$, $SbCl_6^-$," to -- $BF_4$-, $PF_6$-, $SbCl_6$-, --.  
Line 65, change "$AsCl_6^-$, $SbF_6^-$, $AsF_6^-$ or $BR_4^{4-}$," to -- $AsCl_6$-, $SbF_6$-, $AsF_6$- or $BR^4_4{}^-$, --.

Column 14:  
Line 1, change "$MeC_6H_4SO_3$," to -- $MeC_6H_4SO_3^-$, --.  
Line 49, change "BF4-, PF6-, SbCl6-," to -- $BF_4$-, $PF_6$-, $SbCl_6$-, --.  
Line 50, change "AsCl6-, SbF6-, AsF6- or $BR_4^{4-}$," to -- $AsCl_6$-, $SbF_6$-, $AsF_6$- or $BR^4_4{}^-$, --.  
Line 53, change "BF4-," to -- $BF_4$-, --.  
Line 54, change "PF6-," to -- $PF_6$-, --; and change "Cl." to -- Cl$^-$ --.

Signed and Sealed this  
Second Day of October, 2012

David J. Kappos  
*Director of the United States Patent and Trademark Office*